United States Patent [19]

Suzuki et al.

[11] Patent Number: 5,120,737
[45] Date of Patent: Jun. 9, 1992

[54] HEXITOL DERIVATIVES

[75] Inventors: Fumio Suzuki, Mishima; Hiroaki Hayashi; Kazuhiro Kubo, both of Shizuoka; Junichi Ikeda, Mishima, all of Japan

[73] Assignee: Kyowa Hakko Kogyo Co., Ltd., Tokyo, Japan

[21] Appl. No.: 764,827

[22] Filed: Sep. 24, 1991

[30] Foreign Application Priority Data

Sep. 28, 1990 [JP] Japan .................. 2-259385

[51] Int. Cl.$^5$ .................. C07D 487/00; A61K 31/495
[52] U.S. Cl. .................. 514/254; 544/377; 544/360; 544/364
[58] Field of Search .................. 544/377, 360, 364; 514/254

[56] References Cited

U.S. PATENT DOCUMENTS 4,363,805 12/1982 Klessing et al. .................. 424/230
4,806,542 2/1989 Stoss et al. .................. 544/317
5,053,408 10/1991 Suzuki et al. .................. 544/377

OTHER PUBLICATIONS

The Merck Index, 11th Edition (1989), pp. 5113, 5114.

Primary Examiner—Cecilia Shen
Attorney, Agent, or Firm—Fitzpatrick, Cella, Harper & Scinto

[57] ABSTRACT

A hexitol derivative represented by formula (I)

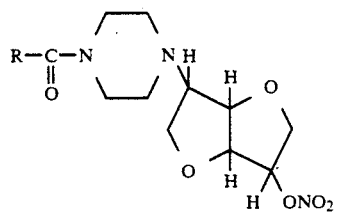

wherein R represents hydrogen, unsubstituted or lower alkyl-substituted cycloalkyl, lower alkenyl, lower alkoxy, lower alkanoyl, piperidyl or

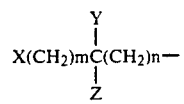

wherein each of m and n independently represents an integer of 0 to 3; each of X, Y and Z independently represents hydrogen, lower alkyl, lower alkoxy, lower alkanoyl, lower alkanoyloxy, hydroxyl, halogen or nitro or a pharmaceutically acceptable salt thereof.

14 Claims, No Drawings

HEXITOL DERIVATIVES

BACKGROUND OF THE INVENTION

The present invention relates to deoxy-1.4;3.6-dianhydrohexitol nitric acid esters having a vasodilative activity.

As hexitol derivatives having pharmacological activities, there are known isosorbide as a diuretic [The Merck Index, 11th edition, page 5113 (1989)] and isosorbide dinitrate as a coronary dilator [The Merck Index, 11th edition, page 5114 (1989)].

Further in connection with the present invention, 5-(4-methylpiperazin-1-yl)-5-deoxy-1.4;3.6-dianhydro-L-iditol 2-nitrate showing a vasodilatory activity is disclosed in Japanese Published Unexamined Patent Application No. 58686/82 [U.S. Pat. No. 4,363,805 and EP-A-44940].

Organic nitrates, for example, nitroglycerine have been clinically used for angina pectoris. Because of poor oral absorption, however, it is impossible to use nitroglycerine for preventive therapy for attacks of angina pectoris and the administration of nitroglycerine is always limited to emergency care or attacks of angina pectoris in sublingual administration. On the other hand, it has been known that hexitol derivatives, e.g. isosorbide dinitrate are useful in the treatment of angina pectoris or coronary deficiency but its therapeutic effects were not enough in view of the pharmacological activities and side effects such as headache, vomiting, etc. In addition, they are explosive and should thus be handled carefully.

SUMMARY OF THE INVENTION

According to the present invention, there are provided nitric acid esters of substituted piperazino-1.4;3.6-dianhydrohexitols having excellent oral absorption property and having a potent anti-coronary vasospastic activity.

The present invention relates to hexitol derivatives represented by formula (I):

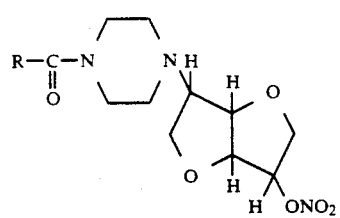
(I)

wherein R represents hydrogen, unsubstituted or lower alkyl-substituted cycloalkyl, lower alkenyl, lower alkoxy, lower alkanoyl, piperidyl or

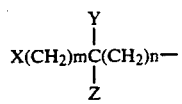

wherein each of m and n independently represents an integer of 0 to 3; each of X, Y and Z independently represents hydrogen, lower alkyl, lower alkoxy, lower alkanoyl, lower alkanoyloxy, hydroxyl, halogen or nitro, or pharmaceutically acceptable salts thereof.

DETAILED DESCRIPTION OF THE INVENTION

Hereafter compounds represented by formula (I) are referred to as Compound (I). With respect to compounds represented by other formula numbers, the same rule applies.

In the definition of R in formula [I], the cycloalkyl and the cycloalkyl moiety in the lower alkyl-substituted cycloalkyl have 3 to 6 carbon atoms, such as cyclopropyl, cyclobutyl, cyclopentyl, cyclohexyl, etc. The lower alkenyl means a straight or branched alkenyl having 2 to 6 carbon atoms, for example, vinyl, allyl, methacryl, crotyl, etc. The lower alkyl and the alkyl moiety in the lower alkoxy mean a straight or branched alkyl having 1 to 6 carbon atoms, for example, methyl, ethyl, propyl, isopropyl, butyl, isobutyl, sec-butyl, tert-butyl, pentyl, neopentyl, hexyl, etc. The lower alkanoyl and the alkanoyl moiety in the lower alkanoyloxy mean a straight or branched alkanoyl having 1 to 6 carbon atoms, for example, formyl, acetyl, propionyl, butyryl, isobutyryl, valeryl, isovaleryl, pivaloyl, hexanoyl, etc. The halogen includes for example, fluorine, chlorine, bromine and iodine.

The pharmaceutically acceptable salt of Compound (I) includes an inorganic acid addition salt such as hydrochloride, sulfate, phosphate, etc. and an organic acid addition salt such as acetate, maleate, fumarate, tartarate, citrate, etc.

Processes for preparing Compound (I) are described below.

Process 1

Compound (I) can be obtained by reacting Compound (II) with Compound (III).

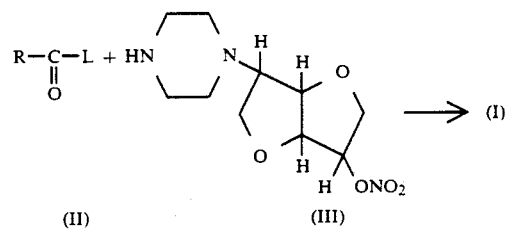

wherein R has the same significance as described above; and L represents a leaving group.

The leaving group denoted by L includes, for example, halogen such as chlorine, bromine, iodine, etc.; alkylsulfonyloxy such as methanesulfonyloxy, etc.; arylsulfonyloxy such as phenylsulfonyloxy, p-toluenesulfonyloxy, etc.; alkoxycarbonyloxy such as tert-butoxycarbonyloxy, ethoxycarbonyloxy, isobutoxycarbonyloxy, etc.

The reaction is performed in a solvent, preferably in the presence of a base. Any solvent may be used so long as it is inert to the reaction. The solvent includes, for example, ethers such as tetrahydrofuran, dioxane, etc.; fatty acid dimethylamides such as dimethylformamide, dimethylacetamide, etc.; ketones such as acetone, methyl ethyl ketone, etc.; alcohols such as methanol, ethanol, isopropyl alcohol, etc.; halogenated hydrocarbons such as methylene chloride, chloroform, dichloroethane, etc.; esters such as ethyl acetate, etc.; and dimethylsulfoxide, etc. These solvents are used alone or in combination.

The base used includes, for example, an alkali metal bicarbonate such as sodium bicarbonate, potassium bicarbonate, etc.; an alkali metal carbonate such as sodium carbonate, potassium carbonate, etc.; an alkali metal hydride such as sodium hydride, etc.; an alkali metal alkoxide such as sodium methoxide, sodium ethoxide, etc.; an ammonium salt such as trimethyl benzyl ammonium hydroxide (Triton B), etc.; an organic base such as triethylamine, pyridine, etc.

The reaction temperature is in the range of −30° to 150° C., preferably from −10° to 100° C. The reaction is completed from 5 minutes to 20 hours.

The starting Compound (III) can be synthesized basically according to the methods described in Reference Examples and the starting Compound (II) can be synthesized from the corresponding carboxylic acid by known methods generally used in organic synthetic chemistry.

Process 2

Compound (I) can be obtained by reacting Compound (IV) with Compound (III) in the same manner as in Process 1.

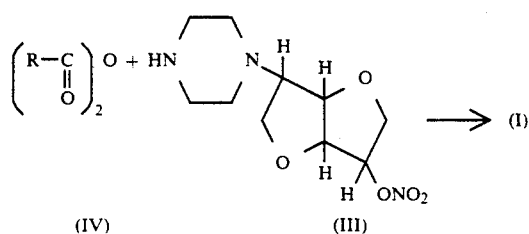

wherein R has the same significance as described above.

Process 3

Compound (I) can be obtained by reacting Compound (V) with a nitrating agent in the presence or absence of a solvent:

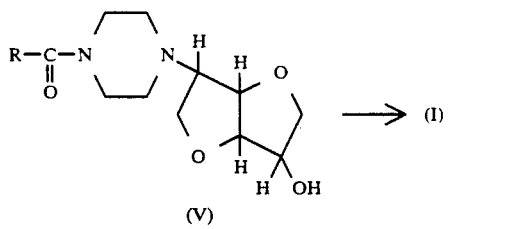

wherein R has the same significance as described above.

As the nitrating agent, there may be used, for example, acetic anhydride-fuming nitric acid, fuming nitric acid, fuming nitric acid-conc. sulfuric acid, etc. As the solvent, acetonitrile, chloroform, methylene chloride, acetic acid, etc. are preferably used.

The reaction is performed at −40° to 20° C. and completed from 30 seconds to 5 hours, although the reaction time varies depending upon the reaction temperature.

Compound (V) can be prepared according to Process 1 or Process 2, using the compounds obtained in Reference Examples.

The intermediates and the objective compounds in these processes described above can be isolated and purified by purification methods conventionally used in organic synthetic chemistry, for example, filtration, extraction, washing, drying, concentration, recrystallization, various column chromatographies, etc. The intermediates may also be provided in the subsequent reaction, without being particularly purified.

In case that salts of Compound (I) are desired to be obtained, when Compound [I] is obtained in the form of a salt, Compound (I) may be purified as it is. Further in case that Compound (I) is obtained in a free form, salts may be formed in a conventional manner.

Compound (I) and pharmaceutically acceptable salts thereof may also be present in the form of addition products to water or various solvents; in this case, the addition products are also included in the present invention.

Specific examples of Compound [I] are shown in Table 1.

TABLE 1

| Compound No. (Example) | R |
|---|---|
| 1 (1) | $CH_3-$ |
| 2 (2) | $CH_3CH_2-$ |
| 3 (3) | $CH_3(CH_2)_2-$ |
| 4 (4) | $(CH_3)_2CH-$ |
| 5 (5) | $CH_3(CH_2)_3-$ |
| 6 (6) | $(CH_3)_2CHCH_2-$ |
| 7 (7) | $CH_3(CH_2)_5-$ |
| 8 (8) | cyclohexyl |
| 9 (9) | piperidinyl (N-H) |
| 10 (10) | $CH_3CH_2CH(CH_3)-$ |
| 11 (11) | $(CH_3CH_2)(CH_3CH_2)CH-$ |
| 12 (12) | $CH_3OCH_2-$ |
| 13 (13) | $CH_3CO-O-CH(CH_2CH_3)-$ |
| 14 (14) | $CH_3CH_2CH(OH)-$ |
| 15 (15) | $CH_3CH_2CH(Cl)-$ |
| 16 (16) | $ClCH_2CH_2CH_2-$ |
| 17 (17) | $CH_3CH_2CH(Br)-$ |

TABLE 1-continued

R—C(=O)—N(piperidine)—N(H)—...—ONO₂ (structure with R-C(=O)-N group attached to piperidine linked to bicyclic system with ONO₂)

| Compound No. (Example) | R |
|---|---|
| 18 (18) | $(CH_3)_3C-$ |
| 19 (19) | $BrCH_2CH_2CH_2-$ |
| 20 (20) | $(E)-CH_3CH=CH-$ |
| 21 (21) | $O_2NCH_2CH_2-$ |
| 22 (22) | $(CH_3)_3CCH_2-$ |
| 23 (23) | $CH_3CH_2C(CH_3)_2-$ |
| 24 (24) | $CH_3CH(Cl)-$ |
| 25 (25) | 1-methylcyclopropyl ($CH_3$-cyclopropyl) |
| 26 (26) | cyclopropyl |
| 27 (27) | $CH_3C(=O)-$ |
| 28 (28) | $CH_2=CHCH_2-$ |
| 29 (29) | $CH_2=CH(CH_3)-$ |
| 30 (30) | $(E)-CH_3CH=C(CH_3)-$ |
| 31 (31) | $(CH_3)_2C=CH-$ |
| 32 (32) | $(CH_3)_2CHCH_2O-$ |

Pharmacological effects of Compound (I) are illustrated in (a) a test for coronary vasospasm model, (b) a test for heart failure model and (c) a test for acute toxicity model.

Experiment (a) Effects on coronary vasospasm model (lysine-vasopressin test)

Male Wistar rats weighing 200 to 250 g were used as experimental animals. Electrocardiogram (ECG) was measured by electrocardiograph (RB-5, Nihon Koden) and recorded on polygraph (RPM-6200; Nihon Koden).

Oral and intraperitoneal administrations of test compounds to rats were performed 30 and 20 minutes before the anesthetization, respectively. After rats were anesthetized with urethane, lysine-vasopressin (V-2875, Sigma) was intravenously injected to rats in a dose of 0.3 I.U./kg for the purpose of inducing coronary vasospasm. After the lysine-vasopressin injection, increase of ST-segment was observed in ECG [Arzneim. Forsch., 36, 1454 (1986)].

In this test, the inhibitory effect of ST-segment elevation following the lysine-vasopressin injection was regarded as anti-angina pectoris activity [Arzneim. Forsch., 36, 1454 (1986)]. The ST-segment heights were measured before and at 20 to 30 seconds after the lysine-vasopressin injection in rats with and without test compound treatment, and then the elevation of ST-segment was calculated in each rat. Inhibition (%) was calculated from the following equation.

$$\text{Inhibition rate (\%)} = \left[1 - \frac{\text{ST-segment elevation rate of test compounds-treated group}}{\text{ST-segment elevation rate of test compounds-untreated group}}\right] \times 100$$

In this test, the compounds which have the inhibition rate of 20% or higher were defined as effective in the coronary vasospasm model and the compounds are considered to have anti-vasospasm activity. The minimum dose for showing the anti-vasospasm activity was defined as the minimum effective dose [MED].

The results are shown in Table 2.

(b) Effects on propranolol-induced heart failure model

Adult mongrel dogs of either sex, weighing from 8 to 20 kg were used for the experiment. The animals were anesthetized with sodium pentobarbital (35 mg/kg iv) and the lungs were ventilated with respirator (made by Takashima Co., for big animals) following tracheal intubation. The common carotid artery was cannulated and the catheter (Millar Tip 5F ® for measurement of the left ventricular pressure was advanced to the left ventricular cavity. Left ventricular pressure (LVP), the maximum rate of change of left ventricular pressure (Max dp/dt) and left ventricular end-diastolic pressure (LVEDP) were measured by the Millar Tip transducer. The systemic blood pressure (BP) was measured with a pressure transducer (MPU-0.5, Nihon Koden) attached to a catheter placed in the femoral artery, and heart rate (HR) was measured with a heart rate meter (AT610-G, Nihon Koden) from BP. All measurements were recorded on a polygraph (RPM-6200, Nihon Koden) or a pen-recorder (RAT-1200, Nihon Koden).

After the values of all parameters were stabilized, a bolus intravenous injection of propranolol at a dose of 2 mg/kg was performed. Thereafter, an intravenous infusion of propranolol (0.05 mg/kg/min.) was carried out to evoke heart failure [J. Cardiovasc. Pharmacol., 6, 35–42 (1984)]. LVEDP was increased by 10 to 15 mmHg as a symptom of heart failure. After occurrence of heart failure, the test compounds were intravenously or intraduodenally administered. After administration of the test compounds, LVEDP, LVP, Max dp/dt, BP and HR were recorded on interval of every 15 minutes.

In this experiment, LVEDP elevation was used as an index of heart failure and the compounds which decrease LVEDP [10 to 15 mmHg] by 20% or more were defined as effective.

The results are shown in Table 2.

TABLE 2

| Compound No. | Coronary vasoconstriction model MED (mg/kg) | | Heart failure model Effective dose (mg/kg) | |
|---|---|---|---|---|
| | i.p. | p.o. | i.d. | i.v. |
| 1Sa* | | <30 | 0.1 | |
| 2Sa | <30 | | | |
| 3Sa | | <30 | 0.3 | 0.1 |
| 4Sa | <30 | | | |
| 5Sa | <30 | | | |
| 6Sa | <30 | | | |
| 7Sa | <30 | | | |
| 8Sa | <30 | | | |
| 10Sa | <30 | | 0.1 | |

TABLE 2-continued

| Compound No. | Coronary vasoconstriction model MED (mg/kg) | | Heart failure model Effective dose (mg/kg) | |
|---|---|---|---|---|
| | i.p. | p.o. | i.d. | i.v. |
| 15Sa | | <30 | | |
| 16Sa | <25 | <30 | | |
| 19Sa | | <30 | | |
| 20Sa | <25 | | | |
| 22Sa | <25 | | | |
| 25Sa | | <30 | | |
| 26Sa | | <30 | 0.3 | |
| 27Sa | <25 | <30 | | |
| 28Sa | <25 | | 0.3 | |

*Sa denotes the hydrochloride of the compound.

(c) Acute Toxicity

The compounds were orally administered and intraperitoneally administered to male dd-mice wighing 20 to 25 g. Minimum effective dose (MED) was determined by observing the mortality for seven days after the administration.

The results are shown in Table 3.

TABLE 3

| Compound No. | MLD (mg/kg) | |
|---|---|---|
| | i.p. | p.o. |
| 3Sa | >100 | >300 |
| 7Sa | >100 | >300 |
| 10Sa | >100 | >300 |
| 15Sa | >100 | >300 |
| 16Sa | >100 | >300 |
| 20Sa | >100 | >300 |
| 22Sa | >100 | >300 |
| 25Sa | >100 | >300 |
| 26Sa | >100 | >300 |

Compound (I) or pharmaceutically acceptable salts thereof may be used as they are or in the form of various medical preparations. The medical preparation of the present invention can be prepared by uniformly mixing, as an active ingredient, an effective dose of Compound (I) or pharmaceutically acceptable salts thereof with pharmaceutically acceptable carriers. These medical compositions are desirably in the form of unit dose suited for oral or parenteral administration.

In preparing compositions which are in the form suitable for oral administration, any useful pharmaceutically acceptable carriers can be used. A liquid preparation suited for oral administration, for example, an emulsion and a syrup can be prepared using water; sugars such as sucrose, sorbitol, fructose, etc.; glycols such as polyethylene glycol, propylene glycol, etc.; oils such as sesame oil, olive oil, soybean oil, etc.; antiseptics such as an alkyl p-hydroxybenzoate,.etc.; flavors such as strawberry flavor, pepper mint, etc. Furthermore, a powder, a pill, a capsule and a tablet can be prepared by using an excipient such as lactose, glucose, sucrose, mannitol, etc.; a disintegrator such as starch, sodium alginate, etc.; a lubricant such as magnesium stearate, talc, etc.; a binder such as polyvinyl alcohol, hydroxypropyl cellulose, gelatin, etc.; a surfactant such as a fatty acid ester, etc.; a plasticizer such as glycerine, etc. A tablet and a capsule are the most useful unit preparations for oral administration since their administration is easy. Upon preparing the tablet and capsule, individual pharmaceutical carriers are used. A solution for injection can be prepared by using distilled water, a saline, a glucose solution or carrier composed of a saline and a glucose solution. Effective dose and number of administration of Compound (I) or pharmaceutically acceptable salts thereof vary depending upon mode of administration, age, body weight, conditions, etc. of the patient but daily dose is generally 0.1 to 50 mg/kg and the number of administration per day may be divided into 3 to 4 times.

Hereafter, the present invention is described by referring to Examples, Reference Examples and Pharmaceutical Preparation below.

EXAMPLE 1

5-(4-Acetylpiperazin-1-yl)-5-deoxy-1.4;3.6-dianhydro-L-iditol 2-nitrate (Compound 1)

A mixture of 2.00 g (7.71 mmols) of Compound b obtained in Reference Example 2 and 30 ml of methylene chloride was stirred at 0° C. 0.73 ml (7.74 mmols) of acetic anhydride and 0.62 ml (7.67 mmols) of pyridine were dropwise added to the mixture in sequence. The mixture was stirred at 0° C. for further 30 minutes. After the reaction, an aqueous sodium bicarbonate was added to the solution, the mixture was extracted with methylene chloride. The methylene chloride layer was dried over anhydrous sodium sulfate and the solvent was evaporated under reduced pressure. The residue was purified by silica gel column chromatography (eluent: chloroform/methanol = 30/1) to give Compound 1.

Chloroform was added to dissolve Compound 1 and ethyl acetate saturated with hydrogen chloride was added to the resulting solution. The mixture was poured into cold diethyl ether and the precipitated crystals were filtered and dried to give 2.57 g (yield, 99%) of the hydrochloride of Compound 1.

Melting point: 137.0-140.0° C.
MS(EI) m/e: 301(M$^+$)
IR(KBr) cm$^{-1}$: 1658, 1640, 1434, 1279, 1083, 856
NMR(DMSO-d$_6$)δ(ppm): 5.44(1H, m), 5.27(1H, m), 4.84 (1H, m), 2.70-4.65(13H, m), 2.04 (3H, s)

EXAMPLE 2

5-Deoxy-5-(4-propionylpiperazin-1-yl)-1.4;3.6-dianhydro-L-iditol 2-nitrate (Compound 2)

Compound 2 was obtained as the hydrochloride (yield, 80%) in a similar manner to Example 1 except that propionic anhydride was used in place of acetic anhydride and that the stirring period was changed from 30 minutes to an hour and 30 minutes.

MS(EI) m/e: 315(M$^+$)
IR(KBr) cm$^{-1}$: 1660, 1644, 1435, 1278, 1083, 857
NMR(DMSO-d$_6$)δ(ppm): 5.44(1H, m), 5.31(1H, m), 4.83 (1H, m), 2.75-4.75(13H, m), 2.36(2H, q, J=7.5 Hz), 0.99(3H, t, J=7.5 Hz)

EXAMPLE 3

5-(4-Butyrylpiperazin-1-yl)-5-deoxy-1.4;3.6-dianhydro-L-iditol 2-nitrate (Compound 3)

Compound 3 was obtained as the hydrochloride (yield, 79%) in a similar manner to Example 1 except that butyric anhydride was used in place of acetic anhydride and that the stirring period was changed from 30 minutes to an hour and 30 minutes.

Melting point: 113.5-114.0° C.
MS(EI) m/e: 329(M$^+$)
IR(KBr) cm$^{-1}$: 1657, 1641, 1431, 1277, 1082, 853
NMR(DMSO-d$_6$)δ(ppm) 5.44(1H, m), 5.29(1H, m), 4.84 (1H, m), 2.80-4.70(13H, m), 2.33(2H, t, J=7.4 Hz), 1.52(2H, m), 0.90(3H, t, J=7.3 Hz)

EXAMPLE 4

5-Deoxy-5-(4-isobutyrylpiperazin-1-yl)-1.4;3.6-dianhydro-L-iditol 2-nitrate (Compound 4)

Compound 4 was obtained as the hydrochloride yield, 87%) in a similar manner to Example 1 except that isobutyric anhydride was used in place of acetic anhydride and that the stirring period was changed from 30 minutes to an hour and 30 minutes.

Melting point: 140.5–141.0° C.

Elemental analysis: as $C_{14}H_{23}N_3O_6 \cdot HCl$ Calcd. (%): C 45.97, H 6.61, N 11.49 Found (%): C 45.84, H 6.77, N 11.52

IR(KBr) cm$^{-1}$: 1659, 1644, 1436, 1276, 1089, 996, 854

NMR(DMSO-d$_6$)δ(ppm): 5.44(1H, m), 5.27(1H, m), 4.84 (1H, m), 2.70–4.70(13H, m), 2.89(1H, m), 1.01 (6H, d, J=6.6 Hz)

EXAMPLE 5

5-Deoxy-5-(4-valerylpiperazin-1-yl)-1.4;3.6-dianhydro-L-iditol 2-nitrate (Compound 5)

While stirring a mixture of 2.50 g (24.48 mmols) of valeric acid and 60 ml of methylene chloride at 0° C., 4.40 ml (54.40 mmols) of pyridine and 1.78 ml (24.51 mmols) of thionyl chloride were dropwise added to the mixture in sequence. The mixture was stirred at 0° C. for further an hour (hereafter referred to as Solution A).

A mixture of 2.80 g (10.80 mmols) of Compound b obtained in Reference Example 2 and 30 ml of acetonitrile was stirred at 0° C. and Solution A was dropwise added thereto. The solution mixture was stirred at 0° C. for further 3 hours and concentrated under reduced pressure. Thereafter, an aqueous saturated sodium bicarbonate solution was added to the residue followed by extraction of the solution with chloroform. The extract was dried over anhydrous sodium sulfate. The solvent was evaporated under reduced pressure, and the residue was purified by silica gel column chromatography (Eluent: chloroform/methanol=50/1) to give Compound 5.

Chloroform was added to dissolve Compound 5 and ethyl acetate saturated with hydrogen chloride was added to the solution. The mixture was poured into cold diethyl ether and the precipitated crystals were filtered and dried to give 2.04 g (yield, 50%) of Compound 5 as the hydrochloride.

Melting point: 61.0–61.5° C.

MS(EI) m/e: 343(M+)

IR(KBr) cm$^{-1}$: 1642, 1432, 1276, 1086, 852

NMR(DMSO-d$_6$)δ(ppm): 5.44(1H, m), 5.26(1H, m), 4.83 (1H, m), 2.8–4.6(13H, m), 2.34(2H, t, J=7.3 Hz), 1.48(2H, m), 1.30(2H, m), 0.88(3H, t, J=7.2 Hz)

EXAMPLE 6

5-Deoxy-5-(4-isovalerylpiperazin-1-yl)-1.4;3.6-dianhydro-L-iditol 2-nitrate (Compound 6)

Compound 6 was obtained as the hydrochloride (yield, 58%) in a similar manner to Example 5 except that isovaleric acid was used in place of valeric acid.

Melting point: 181.5–183.0° C.

MS(EI) m/e: 343(M+)

IR(KBr) cm$^{-1}$: 1658, 1641, 1432, 1279, 1087, 851

NMR(DMSO-d$_6$)δ(ppm): 5.44(1H, m), 5.26(1H, m), 4.83 (1H, m), 2.8–4.3(13H, m), 2.23(2H, d, J=7.0 Hz), 1.98(1H, m), 0.91(6H, d, J=6.6 Hz)

EXAMPLE 7

5-Deoxy-5-(4-heptanoylpiperazin-1-yl)-1.4;3.6-dianhydro-L-iditol 2-nitrate (Compound 7)

Compound 7 was obtained as the hydrochloride (yield, 66%) in a similar manner to Example 1 except that heptanoic anhydride was used in place of acetic anhydride and that the reaction condition was changed from at 0° C. for 30 minutes to at room temperature for 4 hours.

Melting point: 178.0–178.5° C.

Elemental analysis: as $C_{17}H_{29}N_3O_6 \cdot HCl$ Calcd. (%): C 50.06, H 7.41, N 10.30 Found (%): C 49.87, H 7.49, N 10.28

IR(KBr) cm$^{-1}$: 1658, 1644, 1433, 1282, 1087, 855

NMR(DMSO-d$_6$)δ(ppm): 5.44(1H, m), 5.26(1H, m), 4.83 (1H, m), 2.75–4.30(13H, m), 2.33(2H, t, J=7.4 Hz), 1.49(2H, m), 1.10–1.45(6H, m), 0.87(3H, t, J=6.8 Hz)

EXAMPLE 8

5-(4-Cyclohexylcarbonylpiperazin-1-yl)-5-deoxy-1.4;3.6-dianhydro-L-iditol 2-nitrate (Compound 8)

Compound 8 was obtained as the hydrochloride (yield, 34%) in a similar manner to Example 5 except that cyclohexanecarboxylic acid was used in place of valeric acid.

Melting point: 141.0–141.5° C.

Elemental analysis: as $C_{17}H_{27}N_3O_6 \cdot HCl$ Calcd. (%): C 50.31, H 6.95, N 10.35 Found (%): C 50.10, H 7.15, N 10.32

IR(KBr) cm$^{-1}$: 1651, 1645, 1435, 1283, 1083, 858

NMR(DMSO-d$_6$)δ(ppm): 5.44(1H, m), 5.26(1H, m), 4.83 (1H, m), 2.70–4.70(13H, m), 2.59(1H, m), 1.46–1.82(4H, m), 0.96–1.46(6H, m)

EXAMPLE 9

5-Deoxy-5-(4-nipecotylpiperazin-1-yl)-1.4;3.6-dianhydro-L-iditol 2-nitrate (Compound 9)

5-[4-(1-t-Butoxycarbonylpiperidin-3-yl-carbonyl)-piperazin-1-yl]-5-deoxy-1.4;3.6-dianhydro-L-iditol 2 nitrate (yield, 37%) was obtained in a similar manner to Example 5 except that Compound c obtained in Reference Example 3 was used in place of valeric acid.

A mixture of 1.80 g (3.83 mmols) of the above compound, 20 ml of ethanol and 20 ml of an aqueous 1N hydrochloric acid solution was stirred at room temperature for 6 days. After concentration under reduced pressure, the residue was trityrated with ethyl acetate. The crystals were filtered and dried to give 1.33 g (yield, 78%) of Compound 9 as the hydrochloride.

MS(FAB) m/e: 371(M+ +1)

IR(KBr) cm$^{-1}$: 1642, 1441, 1278, 1088, 857

NMR(DMSO-d$_6$)δ(ppm): 5.45(1H, m), 5.31(1H, m), 4.85 (1H, m), 2.7–4.6(18H, m), 1.45–1.95(4H, m)

EXAMPLE 10

5-Deoxy-5-[4-(2-methylbutyryl)piperazin-1-yl]-1.4;3.6-dianhydro-L-iditol 2-nitrate (Compound 10)

Compound 10 was obtained as the hydrochloride (yield, 69%) in a similar manner to Example 5 except that 2-methylbutyric acid was used in place of valeric acid.

Melting point: 234.0–234.5° C.

MS(EI) m/e: 343(M+)

IR(KBr) cm$^{-1}$: 1651, 1634, 1462, 1434, 1278, 1088, 857

NMR(DMSO-d$_6$)δ(ppm): 5.44(1H, m), 5.28(1H, m), 4.84 (1H, m), 2.8–4.7(13H, m), 2.72(1H, m), 1.54(1H, m), 1.32(1H, m), 0.99(3H, d, J=6.8 Hz), 0.85(3H, t, J=7.6 Hz)

EXAMPLE 11

5-Deoxy-5-[4-(2-ethylbutyryl)piperazin-1-yl]-1,4;3,6-dianhydro-L-iditol 2-nitrate (Compound 11)

Compound 11 was obtained as the hydrochloride (yield, 75%) in a similar manner to Example 5 except that 2-ethylbutyric acid was used in place of valeric acid.

Melting point: 197.3–197.5° C.
MS(EI) m/e: 357(M+)
IR(KBr) cm$^{-1}$: 1650, 1641, 1461, 1436, 1278, 1229, 1085, 998, 955, 851
NMR(DMSO-d$_6$)δ(ppm): 5.44(1H, m), 5.30(1H, m), 4.83 (1H, m), 2.8–4.4(13H, m), 2.63(1H, m), 1.25–1.65 (4H, m), 0.81(6H, t, J=7.3 Hz)

EXAMPLE 12

5-Deoxy-5-[4-(methoxyacetyl)piperazin-1-yl]-1,4;3,6-dianhydro-L-iditol 2-nitrate (Compound 12)

Compound 12 was obtained as the hydrochloride (yield, 89%) in a similar manner to Example 5 except that methoxyacetic acid was used in place of valeric acid.

Melting point: 126.4–127.5° C.
MS(EI) m/e: 331(M+)
IR(KBr) cm$^{-1}$: 1657, 1643, 1439, 1280, 1114, 958, 857
NMR(DMSO-d$_6$)δ(ppm): 5.44(1H, m), 5.25(1H, m), 4.83 (1H, m), 4.13(2H, s), 3.30(3H, s), 2.75–4.40(13H, m)

EXAMPLE 13

5-[4-(2-Acetoxybutyryl)piperazin-1-yl]-5-deoxy-1,4;3,6-dianhydro-L-iditol 2-nitrate (Compound 13)

A mixture of 5.00 g (48.0 mmols) of 2-hydroxybutyric acid, 4.98 ml (52.8 mmols) of acetic anhydride and 60 ml of pyridine was stirred at 0° C. for 10 minutes. After concentration under reduced pressure, the residue was purified by silica gel column chromatography (eluent; chloroform) to give 7.01 g (yield, 100%) of 2-acetoxybutyric acid.

Thereafter Compound 13 was obtained as the hydrochloride (yield, 45%) in a similar manner to Example 5 except that 2-acetoxybutyric acid was used in place of valeric acid.

Melting point: 125.2–125.7° C.
MS(EI) m/e: 387(M+)
IR(KBr) cm$^{-1}$: 1735, 1660, 1645, 1441, 1376, 1279, 1243, 959, 856
NMR(DMSO-d$_6$)δ(ppm): 5.44(1H, m), 5.15–5.35(2H, m), 4.83(1H, m), 2.80–4.35(13H, m), 2.05(3H, s), 1.70(2H, m), 0.92(3H, t, J=7.3 Hz)

EXAMPLE 14

5-Deoxy-5-[4-(2-hydroxybutyryl)piperazin-1-yl]-1,4;3,6-dianhydro-L-iditol 2-nitrate (Compound 14)

A mixture of 0.65 g (1.68 mmols) of Compound 13 obtained in Example 13, 67 mg (1.68 mmols) of sodium hydroxide, 10 ml of water and 10 ml of tetrahydrofuran was stirred at room temperature for an hour. After concentration under reduced pressure, the residue was purified by silica gel column chromatography (eluent: chloroform/methanol =20/1) to give Compound 14.

Ethanol was added to dissolve Compound 14 and ethyl acetate saturated with hydrogen chloride was added to the resulting solution. The mixture was poured into cold diethyl ether and the precipitated crystals were filtered and dried to give 0.55 g (yield, 86%) of Compound 14 as the hydrochloride.

Melting point: 60.7–72.7° C.
MS(EI) m/e: 345(M+)
IR(KBr) cm$^{-1}$: 3415(br), 1641, 1636, 1439, 1278, 1059, 988, 959, 858
NMR(DMSO-d$_6$)δ(ppm): 5.44(1H, m), 5.27(1H, m), 4.84 (1H, m), 2.7–4.7(15H, m), 1.35–1.80(2H, m), 0.88 (3H, t, J=7.5 Hz)

EXAMPLE 15

5-[4-(2-Chlorobutyryl)piperazin-1-yl]-5-deoxy-1,4;3,6-dianhydro-L-iditol 2-nitrate (Compound 15)

Compound 15 was obtained as the hydrochloride (yield, 79%) in a similar manner to Example 5 except that 2-chlorobutyric acid was used in place of valeric acid.

Melting point: 179.7–179.8° C.
MS(EI) m/e: 363(M+)
IR(KBr) cm$^{-1}$: 1651, 1646, 1441, 1279, 1086, 957, 857
NMR(DMSO-d$_6$)δ(ppm): 5.44(1H, m), 5.28(1H, m), 4.90 (1H, m), 4.84(1H, m), 2.6–4.3(13H, m), 1.65–2.10 (2H, m), 0.96(3H, t, J=7.3 Hz)

EXAMPLE 16

5-[4-(4-Chlorobutyryl)piperazin-1-yl]-5-deoxy-1,4;3,6-dianhydro-L-iditol 2-nitrate (Compound 16)

Compound 16 was obtained as the hydrochloride (yield, 75%) in a similar manner to Example 5 except that 4-chlorobutyric acid was used in place of valeric acid.

Melting point: 159.3–163.9° C.
MS(EI) m/e: 363(M+)
IR(KBr) cm$^{-1}$: 1766, 1643, 1438, 1278, 1086, 998, 959, 858
NMR(DMSO-d$_6$)δ(ppm): 5.44(1H, m), 5.30(1H, m), 4.84 (1H, m), 1.8–4.8(19H, m)

EXAMPLE 17

5-[4-(2-Bromobutyryl)piperazin-1-yl]-5-deoxy-1,4;3,6-dianhydro-L-iditol 2-nitrate (Compound 17)

Compound 17 was obtained as the hydrochloride (yield, 82%) in a similar manner to Example 5 except that 2-bromobutyric acid was used in place of valeric acid.

Melting point: 180.9–181.2° C.
MS(EI) m/e: 407(M+)
IR(KBr) cm$^{-1}$: 1650, 1642, 1440, 1278, 1086, 1000, 958, 857
NMR(DMSO-d$_6$)δ(ppm): 5.44(1H, m), 5.26(1H, m), 4.90 (1H, m), 4.83(1H, m), 2.7–4.3(13H, m), 1.70–2.10 (2H, m), 0.96(3H, t, J=7.3 Hz)

EXAMPLE 18

5-Deoxy-5-(4-pivaloylpiperazin-1-yl)-1,4;3,6-dianhydro-L-iditol 2-nitrate (Compound 18)

Compound 18 was obtained as the hydrochloride (yield, 100%) in a similar manner to Example 5 except that pivaloyl chloride was used in place of Solution A.

Melting point: 204.5–204.7° C.
MS(EI) m/e: 343(M+)
IR(KBr) cm$^{-1}$: 1641, 1631, 1479, 1421, 1366, 1276, 1191, 1087, 995, 955, 855

NMR(DMSO-d$_6$)δ(ppm): 5.44(1H, m), 5.30(1H, m), 4.83 (1H, m), 2.8-4.5(13H, m), 1.20(9H, s)

EXAMPLE 19

5-[4-(4-Bromobutyryl)piperazin-1-yl]-5-deoxy-1.4;3.6-dianhydro-L-iditol 2-nitrate (Compound 19)

Compound 19 was obtained as the hydrochloride (yield, 53%) in a similar manner to Example 5 except that 4-bromobutyric acid was used in place of valeric acid.

MS(EI) m/e: 407(M$^+$)
IR(KBr) cm$^{-1}$: 1658, 1650, 1629, 1576, 1447, 1370, 1322, 1166, 1001, 878, 830, 754
NMR(DMSO-d$_6$)δ(ppm): 5.42(1H, m), 5.11(1H, m), 4.82 (1H, m), 2.0-4.7(19H, m)

EXAMPLE 20

5-(4-Crotonylpiperazin-1-yl)-5-deoxy-1.4;3.6-dianhydro-L-iditol 2-nitrate (Compound 20)

Compound 20 was obtained as the hydrochloride (yield, 91%) in a similar manner to Example 5 except that crotonyl chloride was used in place of Solution A.

Melting point: 175.8-175.9° C.
MS(EI) m/e: 327(M$^+$)
IR(KBr) cm$^{-1}$: 1655, 1642, 1432, 1278, 1232, 1082, 961, 858
NMR(DMSO-d$_6$)δ(ppm): 6.74(1H, m), 6.51(1H, dd, J=14.9 Hz, 1.2 Hz), 5.44(1H, m), 5.28(1H, m), 4.83 (1H, m), 2.6-4.6(13H, m), 1.85(2H, dd, J=6.6 Hz,

EXAMPLE 21

5-Deoxy-5-[4-(3-nitropropionyl)piperazin-1-yl]-1.4;3.6-dianhydro-L-iditol 2-nitrate (Compound 21)

Compound 21 was obtained as the hydrochloride (yield, 75%) in a similar manner to Example 5 except that 3-nitropropionic acid was used in place of valeric acid.

Melting point: 209.8-210.8° C.
MS(EI) m/e: 360(M$^+$)
IR(KBr) cm$^{-1}$: 2916, 1660, 1647, 1560, 1471, 1440, 1417, 1379, 1279, 1234, 1213, 1145, 1086, 1035, 999, 974, 858
NMR (DMSO-d$_6$)δ(ppm): 5.44(1H, m), 5.27(1H, m), 4.84 (1H, m), 4.71(2H, t, J=5.7 Hz), 3.08(2H, t, J=5.7 Hz), 2.7-4.4(13H, m)

EXAMPLE 22

5-Deoxy-5-[4-(3,3-dimethylbutyryl)piperazin-1-yl]-1.4;3.6-dianhydro-L-iditol 2-nitrate (Compound 22)

Compound 22 was obtained as the hydrochloride (yield, 81%) in a similar manner to Example 5 except that 3,3-dimethylbutyric acid was used in place of valeric acid.

Melting point: 272.0-278.0° C.
MS(EI) m/e: 357(M$^+$)
IR(KBr) cm$^{-1}$: 1651, 1633, 1427, 1374, 1285, 1241, 1090, 1033, 965, 848
NMR(DMSO-d$_6$)δ(ppm): 5.44(1H, m), 5.31(1H, m), 4.84 (1H, m), 2.9-4.4(13H, m), 2.27(2H, s), 1.28(9H, s)

EXAMPLE 23

5-Deoxy-5-[4-(2,2-dimethylbutyryl)piperazin-1-yl]-1.4;3.6-dianhydro-L-iditol 2-nitrate (Compound 23)

Compound 23 was obtained as the hydrochloride (yield, 86%) in a similar manner to Example 5 except that 2,2-dimethylbutyric acid was used in place of valeric acid.

Melting point: 197.2-198.0° C.
MS(EI) m/e: 357(M$^+$)
IR(KBr) cm$^{-1}$: 1641, 1636, 1417, 1276, 1089, 994, 954, 854
NMR(DMSO-d$_6$)δ(ppm): 5.44(1H, m), 5.29(1H, m), 4.83(1H, m), 2.8-4.4(13H, m), 1.58(2H, q, J=7.4 Hz), 1.16 (6H, s), 0.80(3H, t, J=7.4 Hz)

EXAMPLE 24

5-[4-(2-Chloropropionyl)piperazin-1-yl]-5-deoxy-1.4;3.6-dianhydro-L-iditol 2-nitrate (Compound 24)

Compound 24 was obtained as the hydrochloride (yield, 93%) in a similar manner to Example 5 except that 2-chloropropionic acid was used in place of valeric acid.

Melting point: 165.7-167.4° C.
MS(EI) m/e: 349(M$^+$)
IR(KBr) cm$^{-1}$: 1 1658, 1640, 1466, 1437, 1375, 1277, 1199, 1067, 992, 956, 852
NMR(DMSO-d$_6$)δ(ppm): 5.43[1H, m), 5.26[1H, m), 5.10 (1H, q, J=6.4 Hz), 4.84(1H, m), 2.7-4.6(13H, m), 1.52(3H, d, J=6.4 Hz)

EXAMPLE 25

5-Deoxy-5-[4-(2-methylcyclopropylcarbonyl)piperazin-1-yl]-1.4;3.6-dianhydro-L-iditol 2-nitrate (Compound 25)

Compound 25 was obtained as the hydrochloride (yield, 81%) in a similar manner to Example 5 except that 2-methylcyclopropanecarboxylic acid was used in place of valeric acid.

Melting point: 172.7-177.1° C.
MS(EI) m/e: 341(M$^+$)
IR(KBr) cm$^{-1}$: 1 1641, 1637, 1466, 1433, 1277, 1234, 1081, 988, 958, 853
NMR(DMSO-d$_6$)δ(ppm): 5.44(1H, m), 5.29(1H, m), 4.84 (1H, m), 2.7-4.6(13H, m), 1.76(1H, m), 1.15[1H, m), 1.07(3H, d, J=5.6 Hz), 0.95(1H, m), 0.58[1H, m)

EXAMPLE 26

5-(4-Cyclopropylcarbonylpiperazin-1-yl)-5-deoxy-1.4;3.6-dianhydro-L-iditol 2-nitrate (Compound 26)

Compound 26 was obtained as the hydrochloride (yield, 85%) in a similar manner to Example 5 except that cyclopropanecarboxylic acid was used in place of valeric acid.

Melting point: 139.5-142.0° C.
MS(EI) m/e: 327(M$^+$)
IR(KBr) cm$^{-1}$: 1642, 1636, 1462, 1436, 1381, 1280, 1235, 1086, 957, 855
NMR(DMSO-d$_6$)δ(ppm): 5.44(1H, m), 5.29(1H, m), 4.85 (1H, m), 2.8-4.6(13H, m), 2.01(1H, m), 0.55-0.95 (4H, m)

EXAMPLE 27

5-Deoxy-5-[4-(2-oxopropionyl)piperazin-1-yl]-1.4;3.6-dianhydro-L-iditol 2-nitrate (Compound 27)

Compound 27 was obtained as the hydrochloride (yield, 42%) in a similar manner to Example 5 except that pyruvic acid was used in place of valeric acid.

Melting point: 106.0-106.5° C.
MS(EI) m/e: 329(M$^+$)
IR(KBr) cm$^{-1}$: 1792, 1651, 1642, 1439, 1280, 1243, 1103, 957, 854

NMR(DMSO-d$_6$)δ(ppm): 5.43(1H, m), 5.24(1H, m), 4.83 (1H, m), 2.8–4.3(13H, m), 2.39(3H, s)

EXAMPLE 28

5-Deoxy-5-(4-vinylacetylpiperazin-1-yl)-1.4;3.6-dianhydro-L-iditol 2-nitrate (Compound 28)

Compound 28 was obtained as the hydrochloride (yield, 42%) in a similar manner to Example 5 except that vinylacetic acid was used in place of valeric acid.
Melting point: 93.0–93.5° C.
MS(EI) m/e: 327(M+)
IR(KBr) cm$^{-1}$: 1640, 1634, 1440, 1278, 1087, 1002, 961, 854
NMR(DMSO-d$_6$)δ(ppm): 5.89(1H, m), 5.44[1H, m), 5.27 (1H, m), 5.14(1H, m), 5.08(1H, m), 4.84(1H, m), 3.21(2H, d, J=6.6 Hz), 2.6–4.7(13H, m)

EXAMPLE 29

5-Deoxy-5-(4-methacryloylpiperazin-1-yl)-1.4;3.6-dianhydro-L-iditol 2-nitrate(Compound 29)

A mixture of 0.39 ml (4.63 mmols) of methacrylic acid, 2.75 ml (19.85 mmols) of triethylamine and 16 ml of a solvent mixture of 2-butanol and acetonitrile (5/1) was stirred at 0° C. A solution of 0.60 ml (4.63 mmols) of isobutyl chloroformate in a solvent mixture of 2-butanol and acetonitrile (5/1) was dropwise added to the reaction mixture followed by stirring at 0° C. for further 5 minutes. Then 1.00 g (3.86 mmols) of Compound b obtained in Reference Example 2 was added thereto, the mixture was stirred at 0° C. for 20 minutes. After concentration under reduced pressure, an aqueous saturated sodium bicarbonate solution was added to the mixture. The mixture was extracted with chloroform. The chloroform layer was dried over anhydrous sodium sulfate and the solvent was evaporated under reduced pressure. The residue was purified by silica gel column chromatography (eluent: chloroform/methanol =50/1) to give Compound 29.

Chloroform was added to dissolve Compound 29 and ethyl acetate saturated with hydrogen chloride was added to the resulting solution. The mixture was poured into cold diethyl ether and the precipitated crystals were filtered and dried to give 0.66 g (yield, 47%) of Compound 29 as the hydrochloride.
Melting point: 172.5–173.5° C.
MS(EI) m/e: 327(M+)
IR(KBr) cm$^{-1}$: 1 1645, 1635, 1462, 1433, 1375, 1277, 1206, 1086, 958, 855
NMR(DMSO-d$_6$)δ(ppm): 5.44(1H, m), 5.27(2H, s), 5.11 (1H, m), 4.85(1H, m), 2.8–4.6(13H, m), 1.87(3H, s)

EXAMPLE 30

5-Deoxy-5-[4-(2-methylcrotonyl)piperazin-1-yl]-1.4;3.6-dianhydro-L-iditol 2-nitrate (Compound 30)

Compound 30 was obtained as the hydrochloride (yield, 30%) in a similar manner to Example 29 except that 2-methylcrotonic acid was used in place of methacrylic acid.
Melting point: 164.5–166.0° C.
MS(EI) m/e: 341(M+)
IR(KBr) cm$^{-1}$: 1642, 1633, 1460, 1427, 1280, 1087, 957, 854
NMR(DMSO-d$_6$)δ(ppm): 5.67(1H, q, J=6.8 Hz), 5.44(1H, m), 5.29(1H, m), 4.84(1H, m), 2.7–4.5(13H, m), 1.74 (3H, s), 1.67(3H, d, J=6.8 Hz)

EXAMPLE 31

5-Deoxy-5-[4-(3,3-dimethylacryloyl)piperazin-1-yl]-1.4;3.6-dianhydro-L-iditol 2-nitrate (Compound 31)

Compound 31 was obtained as the hydrochloride (yield, 68%) in a similar manner to Example 29 except that 3,3-dimethylacrylic acid was used in place of methacrylic acid.
Melting point: 222.0–225.0° C.
MS(EI) m/e: 341(M+)
IR(KBr) cm$^{-1}$: 1641, 1633, 1460, 1427, 1376, 1281, 1245, 1087, 958, 853
NMR(DMSO-d$_6$)δ(ppm): 5.97(1H, s), 5.44(1H, m), 5.30 (1H, m), 4.84(1H, m), 2.8–4.9(13H, m), 1.87(3H, s), 1.82(3H, s)

EXAMPLE 32

5-Deoxy-5-(4-isobutoxycarbonylpiperazin-1-yl]-1.4;3.6-dianhydro-L-iditol 2-nitrate (Compound 32)

Compound 32 was obtained as the hydrochloride (yield, 72%) in a similar manner to Example 29 except that no methacrylic acid was used.
Melting point: 197.4–197.5° C.
MS(EI) m/e: 359(M+)
IR(KBr) cm$^{-1}$: 1 2960, 2415, 1699, 1641, 1468, 1428, 1282, 1250, 1153, 1089, 963, 853
NMR(DMSO-d$_6$)δ(ppm): 5.44(1H, m), 5.27(1H, m), 4.83 (1H, m), 3.82(2H, d, J=6.4 Hz), 2.8–4.3(13H, m), 1.89(1H, m), 0.90(6H, d, J=6.6 Hz)

REFERENCE EXAMPLE 1

5-Deoxy-5-(piperazin-1-yl)-1.4;3.6-dianhydro-L-iditol (Compound a)

A mixture of 20.2 g (90.1 mmols) of 1.4;3.6-dianhydro-D-glucitol 5-methanesulfonate (Japanese Published Unexamined Patent Application No. 58692/82, U.S. Pat. No. 4,542,137 and EP-B-44927), 84.8 g (984.4 mmols) of piperazine and 240 ml of n-butanol was heated under reflux for 36 hours. After concentration under reduced pressure, the residue was azeotropically evaporated with toluene several times to remove piperazine as much as possible Thus, the methanesulfonate of Compound a was obtained as a crude product.

The crude product described above was subjected to chromatography of DIAION SP207 (manufactured by Mitsubishi Kasei Co., Ltd.) (eluent: water~30% aqueous methanol solution). After azeotropic distillation with isopropyl alcohol, crystallization was performed from ethyl acetate to give Compound a in good purity.
NMR(DMSO-d$_6$)δ(ppm): 5.35(1H, m), 4.50(1H, m), 4.19 (1H, m), 2.2–4.1(14H, m)

REFERENCE EXAMPLE 2

5-Deoxy-5-(piperazin-1-yl)-1.4;3.6-dianhydro-L-iditol 2-nitrate (Compound b)

To 37.8 g of the crude methanesulfonate of Compound a obtained in a similar manner to Reference Example 1 was added 10.6 ml of water. While cooling, 5.6 ml of conc. sulfuric acid was dropwise added to the mixture to prepare a solution (hereafter referred to as Solution B).

A solution of 2.47 g (41.1 mmols) of urea in 55.6 ml of conc. sulfuric acid was dropwise added to 37 ml of fuming nitric acid [86%] at −15° C. with stirring. Then, Solution B was dropwise added thereto at −15° C. over 30 minutes to an hour. The mixture was stirred at the same temperature for further 2 hours. The reaction mixture was gradually poured into 300 ml of water with stirring While cooling, a mixture of 120 g [3.00 mmols) of sodium hydroxide and 370 ml of water was gradually added to the solution for neutralization. The solution was extracted with chloroform 5 to 10 times. The chloroform layer was dried over anhydrous sodium sulfate and the solvent was evaporated under reduced pressure. The residue was purified by silica gel column chromatography (eluent: chloroform/methanol=10/1 to 0/1) to give 8.9 g (yield, 38%) of Compound b.

IR(KBr) cm$^-$: 3420(br), 1634, 1278

REFERENCE EXAMPLE 3

1-t-Butoxycarbonylnipecotinic acid (Compound c)

After 5.00 g (38.7 mmols) of nipecotinic acid was added to a mixture of 1.70 g (42.5 mmols) of sodium hydroxide, 40 ml of water and 30 ml of t-butanol, the mixture was stirred at room temperature for dissolution. To the solution was added 8.45 g (38.7 mmols) of di-t-butyl dicarbonate followed by stirring at room temperature for further an hour and 30 minutes. After the reaction, dil. hydrochloric acid was added to adjust pH to 4 and the reaction mixture was extracted with ethyl acetate. The ethyl acetate layer was dried over anhydrous soidum sulfate. The solvent was evaporated under reduced pressure to give 8.87 g [yield, 88%) of Compound c.

Pharmaceutical Preparation 1 Tablet

A tablet comprising the following composition is prepared in a conventional manner.

| Compound 1 | 50 mg |
|---|---|
| Lactose | 150 mg |
| Potato starch | 75 mg |
| Polyvinyl alcohol | 7.5 mg |
| Magnesium stearate | 2.5 mg |

Pharmaceutical Preparation 2 Powder

A powder comprising the following composition is prepared in a conventional manner.

| Compound 1 | 50 mg |
|---|---|
| Lactose | 750 mg |

Pharmaceutical Preparation 3 Syrup

A syrup comprising the following composition is prepared in a conventional manner.

| Compound 1 | 50 mg |
|---|---|
| Refined sugar | 75 mg |
| Ethyl p-hydroxybenzoate | 100 mg |
| Propyl p-hydroxybenzoate | 25 mg |
| Strawberry flavor | 0.25 ml |
| Water is added until the whole volume is 100 ml. | |

Pharmaceutical Preparation 4 Capsule

A capsule comprising the following composition is prepared in a conventional manner.

| Compound 1 | 50 mg |
|---|---|
| Lactose | 500 mg |
| Magnesium stearate | 12.5 mg |

The composition is mixed and the mixture is packed in a gelatin capsule.

Pharmaceutical Preparation 5 Injection

An injection comprising the following composition is prepared in a conventional manner.

| Compound 1 | 20 mg |
|---|---|
| Sodium chloride | 45 mg |

Water is added until the whole volume is 5 ml (corresponding to 1 ampoule)

Water is previously distilled and sterilized in an autoclave.

What is claimed is:

1. A hexitol derivative represented by formula (I)

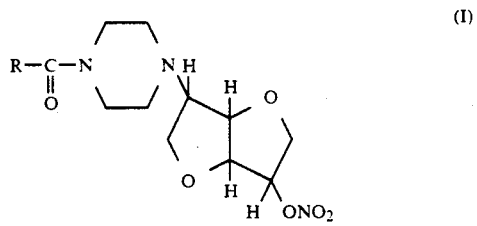

wherein R represents hydrogen, unsubstituted or lower alkyl-substituted cycloalkyl, lower alkenyl, lower alkoxy, lower alkanoyl, piperidyl or

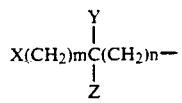

wherein each of m and n independently represents an integer of 0 to 3; each of X, Y and Z independently represents hydrogen, lower alkyl, lower alkoxy, lower alkanoyl, lower alkanoyloxy, hydroxyl, halogen or nitro or a pharmaceutically acceptable salt thereof.

2. A compound according to claim 1, wherein R is unsubstituted or lower alkyl-substituted cycloalkyl.

3. A compound according to claim 2, wherein the unsubstituted or lower alkyl-substituted cycloalkyl is cyclopropyl or 2-methylcyclopropyl.

4. A compound according to claim 1, wherein R is lower alkanoyl.

5. A compound according to claim 4, wherein the lower alkanoyl is acetyl.

6. A compound according to claim 1, wherein R is

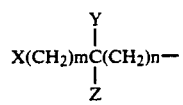

wherein each of m and n independently represents an integer of 0, 1 or 2.

7. A compound according to claim 6, wherein each of X, Y and Z independently represents hydrogen, halogen, or lower alkyl.

8. A compound according to claim 7, wherein each of X, Y and Z is hydrogen, and both of m and n are 1.

9. A compound according to claim 7, wherein each of X, Y and Z is hydrogen, and both of m and n are 0.

10. A compound according to claim 7, wherein each of X and Y is methyl, Z is hydrogen, m is 1 and n is 0.

11. A compound according to claim 7, wherein X is halogen and both of Y and Z represent hydrogen.

12. A compound according to claim 11, wherein X is chlorine, both of m and n are 1.

13. A compound according to claim 1, wherein said salt is an inorganic acid addition salt or an organic acid addition salt.

14. A pharmaceutical composition comprising a pharmaceutical carrier and as an active ingredient, an effective amount of the compound as defined by claim 1.

* * * * *

UNITED STATES PATENT AND TRADEMARK OFFICE
CERTIFICATE OF CORRECTION

PATENT NO. : 5,120,737
DATED : June 9, 1992
INVENTOR(S) : FUMIO SUZUKI, ET AL.

It is certified that error appears in the above-identified patent and that said Letters Patent is hereby corrected as shown below:

COLUMN 13

Line 30, "J = 6.6 Hz," should read --J = 6.6 Hz, 1.2 Hz)--.

COLUMN 14

Line 37, "1 1641," should read --1641,--.
Line 41, "0.58[1H, m)" should read --0.58(1H, m)--.

COLUMN 15

Line 25, "of0.60 ml" should read --of 0.60 ml--.

COLUMN 16

Line 44, "possible" should read --possible.--.

COLUMN 17

Line 3, "stirring" should read --stirring.--.
Line 26, "soidum" should read --sodium--.

UNITED STATES PATENT AND TRADEMARK OFFICE
CERTIFICATE OF CORRECTION

PATENT NO.   : 5,120,737
DATED        : June 9, 1992
INVENTOR(S)  : FUMIO SUZUKI, ET AL.

It is certified that error appears in the above-identified patent and that said Letters Patent is hereby corrected as shown below:

<u>COLUMN 20</u>

Line 2, "chlorine," should read --chlorine, and--.

Signed and Sealed this

Sixteenth Day of November, 1993

*Attest:*

BRUCE LEHMAN

*Attesting Officer*     Commissioner of Patents and Trademarks